United States Patent [19]

Merger et al.

[11] 4,330,479

[45] May 18, 1982

[54] THERMAL DECOMPOSITION OF ARYL URETHANES

[75] Inventors: Franz Merger, Frankenthal; Friedrich Towae, Ludwigshafen, both of Fed. Rep. of Germany

[73] Assignee: BASF Aktiengesellschaft, Ludwigshafen, Fed. Rep. of Germany

[21] Appl. No.: 196,236

[22] Filed: Oct. 14, 1980

[30] Foreign Application Priority Data

Oct. 20, 1979 [DE] Fed. Rep. of Germany ....... 2942543

[51] Int. Cl.$^3$ .......................................... C07C 118/00
[52] U.S. Cl. ................................................ 260/453 P
[58] Field of Search ..................................... 260/453 P

[56] References Cited

U.S. PATENT DOCUMENTS 3,919,279 11/1975 Rosenthal et al. .............. 260/453 P
3,919,280 11/1975 Rosenthal et al. .............. 260/453 P
4,081,472 3/1978 Tsumura et al. ................ 260/453 P Primary Examiner—Dolph H. Torrence
Attorney, Agent, or Firm—H. Lawrence Jones

[57] ABSTRACT

A process for making aryl isocyanates comprises thermally decomposing aryl urethanes at a temperature between 175° C. and 600° C. in the presence of a catalyst, present in the heterogeneous phase, said catalyst being a metal selected from the group consisting of zinc, aluminum, titanium, iron, chromium, cobalt and nickel.

14 Claims, No Drawings

THERMAL DECOMPOSITION OF ARYL URETHANES

BACKGROUND OF THE INVENTION

1. Field of the Invention

This invention relates to a process for making aryl isocyanates such as aryl mono-, di- and polyisocyanates by thermally decomposing aryl urethanes at a temperature between 175° C. and 600° C. in the presence of a catalyst, present in a heterogeneous phase, the catalyst being a metal selected from the group consisting of zinc, aluminum, titanium, iron, chromium, cobalt and nickel. More particularly, the invention relates to the use of a catalyst with a large surface area.

2. Description of the Prior Art

It is part of the current state of the art that N-substituted urethanes can be thermally decomposed in a gas or liquid phase into isocyanates. The thermal decomposition simultaneously produces various undesirable secondary reactions, such as the decarboxylation reaction of urethanes, which may be accompanied by the formation of primary and secondary amines and olefins, the reaction of an isocyanate and a urethane to form an allophanate, the reaction of an isocyanate and an amine to form a urea, and the polymerization of isocyanates into a uretdione and an isocyanurate.

According to data in German Published Application 19 44 719 (British Pat. No. 1,247,451), the thermal decomposition of urethanes in the vapor phase is carried out at temperatures of 400° C. to 600° C. in the presence of a Lewis acid catalyst with the isocyanate and the alcohol being separated by fractional condensation. The vapor phase in this case is defined such that the reaction mixture, possibly including a solvent, is present in the vapor phase following the decomposition independent of feeding as gaseous, liquid or solid urethane. Toluene diisocyanate, for instance, is produced by the pyrolysis of toluene-2,4-diethylurethane in the presence of ferric chloride. Drawbacks of this reaction include low yield combined with considerable quantities of a polymeric byproduct, the decomposition of the catalyst and corrosion of the reaction equipment. German Published Application No. 24 10 505 (U.S. Pat. No. 3,870,739) describes a process where the urethane is decomposed at a temperature of 350° C. to 550° C. and a pressure of less than the (m+1) multiple of the isocyanate vapor pressure of the isocyanate product in a catalyst-free pyrolysis zone within 15 seconds. Drawbacks of this process are that a large quantity of heat must be quickly added to the powdered urethane for the endothermal decomposition, and the separation of a solid polymer byproduct makes the implementation of a continuous process more difficult.

The thermal decomposition of urethanes in the liquid phase is described, for instance, in German Application No. 24 21 503 (U.S. Pat. No. 3,962,302) and German Application No. 25 30 001 (U.S. Pat. No. 3,919,280). According to German Application No. 24 21 503, the urethanes are dissolved in an inert solvent such as alkylbenzene, linear and cyclic hydrocarbons, and/or phthalic acid esters, and are decomposed at atmospheric pressure or above at a temperature of from 175° C. to 350° C. The resultant isocyanate and alcohol are separated and isolated by means of the solvent as entraining agent and/or by using an inert gas as entraining agent. According to German Application No. 25 30 001, higher molecular, substituted or unsubstitied aliphatic, cycloaliphatic, or aromatic hydrocarbons, ether, esters or ketones are used as reaction medium. Only distillation is mentioned for isolating the decomposition products with isocyanate, alcohol and entraining agent being distilled overhead whereas the reaction medium remains as bottom fraction.

For the manufacture of aromatic isocyanates according to German Published Application No. 26 35 490, the urethanes are brought in contact with a solution of at least one metal ion such as ions of copper, zinc, aluminum, tin, titanium, vanadium, iron, cobalt and nickel as catalysts which is dissolved in a solvent having a boiling point of 200° C. in a metal concentration of at least 0.001 percent by weight relative to the solvent at temperatures of 150° C. to 350° C. under reduced pressure. The resultant decomposition products are isolated by fractional condensation.

In accordance with the above-mentioned processes, urethanes, depending upon their structure, can be transformed into isocyanates with, in part, very good yields. These publications do not describe, in the form of examples, the manufacture of mixtures of diphenylmethane diisocyanates and polyphenyl polymethylene polyisocyanates (crude MDI) from the corresponding urethane mixtures (crude MDU). Other than the described isocyanates, crude MDI is not completely distillable by using solvents as entraining agents and can therefore not be isolated as described above from the catalyst, solvent and nonreacted raw materials and impurities.

An object of this invention is to improve the thermal decomposition of aryl urethanes into aryl isocyanates, particularly of high molecular aryl-di- and/or -polyurethanes into aryl-di- and/or -polyisocyanates eliminating the above-mentioned drawbacks.

SUMMARY OF THE INVENTION

An improved process for making aryl isocyanates comprises thermally decomposing aryl urethanes at a temperature between 175° C. and 600° C. in the presence of a catalyst, present in a heterogeneous phase, the catalyst being selected from the group consisting of zinc, aluminum, titanium, iron, chromium, cobalt and nickel. More particularly, the invention relates to the use of a catalyst with a large surface area.

DESCRIPTION OF THE PREFERRED EMBODIMENTS

The metals used in this invention are not only good heat transfer agents, but also good catalysts which facilitates marked decreased in reaction temperature and/or reaction time so that secondary reactions such as polymerizations are less important. Zinc and aluminum have particularly excellent activity in this process. In decomposing aryl diurethanes in the vapor phase, the zinc and aluminum heterogeneous catalysis results in a reduction of the decomposition temperature of from about 50° C. to 100° C. compared with other familiar processes for the same rate of decomposition. Vapor phase decomposition in the sense of this invention, is herein defined such that the decomposition takes place in the vapor phase; liquid phase decomposition is defined such that the decomposition takes place in the liquid phase. Another advantage is that the metals present in the heterogeneous phase can easily be separated from the reaction mixture and can be used again. It is well known that the removal of dissolved catalysts from the reaction product is a problem, particularly when the aryl isocyanates cannot be distilled.

Metals of the series zinc, aluminum, titanium, iron, chromium, cobalt and nickel are suitable for the thermal decomposition of aryl urethanes by heterogeneous catalysis which can take place in the vapor or liquid phase. Zinc and aluminum are preferably used. Also used are alloys of these metals with other metals such as vanadium and/or tungsten.

The catalysts, which in accordance with this invention are present in the reaction mixture in the heterogeneous phase, preferably have a large surface area, for instance, in the form of a metal wool, metal shavings, powders or granules having average particle diameters of 1 millimeter to 10 millimeters, preferably of 2 millimeters to 6 millimeters. The catalysts can be used in various arrangements, for instance, as a fixed bed, such as a tube, tank or vessel reactors charged with metal granules, rings, shavings or wools, so that the reaction mixture can be continuously directed through the fixed bed or as suspensions in an agitator reactor.

For the vapor phase in a fixed bed, the catalysts according to this invention may be charged with 0.1 aryl urethane equivalent per liter of catalyst an hour to 20 aryl urethane equivalents per liter of catalyst an hour, 1 aryl urethane equivalent per liter of catalyst an hour to 10 aryl urethane equivalents per liter of catalyst an hour and for the liquid phase, with 0.1 aryl urethane equivalent per liter of catalyst an hour to 5 aryl urethane equivalents per lier of catalysts an hour, preferably 0.2 aryl urethane equivalent per liter of catalyst an hour to 3 aryl urethane equivalents per liter of catalyst an hour. In suspensions, higher loads than in the fixed bed are sometimes possible.

Solvents used include those which are inert with respect to isocyanates and other components under the reaction conditions and which have a different boiling point than the isocyanates and the other components. A solvent, the boiling point of which is between the boiling points of the aryl isocyanate and the separated alcohol, is advantageous for decompositions in the liquid phase when the aryl isocyanate is isolated as a nondistilled bottom fraction. However, solvents may also be used as a diluting agent for decompositions in the vapor phase and can possibly facilitate easier isolation of the isocyanate by fractional condensation without recombination with the alcohol. A solvent, the boiling point of which is higher than the boiling point of the decomposition products, is preferably used for the decomposition in the liquid phase of aryl urethanes to aryl isocyanates which are isolated by distillation, possibly also by using stripping agents. In order to facilitate an improved isolation of alcohol and isocyanate, a solvent which boils between alcohol and isocyanate may be used. Proven to have worked particularly well and preferably applied for the separation of di- and/or polyurethanes in the liquid phase to aryl-di- and/or -polyisocyanates, is dibenzylnaphthalene, which is available by benzylation of naphthalene and benzyl chloride. It is advantageous if the aryl urethanes are soluble in the solvent, although this is not absolutely essential. The solvent at the same time is a heating medium which serves to supply the reaction system which heat and to maintain a uniform reaction temperature. A solvent may be a mixture of solvents.

Examples of the solvent used include: aliphatic hydrocarbons, such as the higher alkanes, decane, undecane, dodecane, tridecane, tetradecane, pentadecane, hexadecane, heptadecane, liquid paraffin, petroleum fractions of paraffins which are normally used as lubricating oils, cooling oils or cutting oils; alicyclic hydrocarbons such as cycloparaffins; substituted aromatic hydrocarbons such as decahydronaphthalene, naphthalene, 1- and 2-methylnaphthalene, 1,2-, 1,4-, 1,6-, 2,7-, 2,6- and 2,3-dimethylnaphthalene, 1-ethylnaphthalene, phenylnaphthalene, benzylnaphthalene, toluene, 1,2-, 1,3- and 1,4-dimethylbenzene, 1,2,4- and 1,3,5-trimethylbenzene, 1,2,3,5- and 1,2,4,5-tetramethylbenzene, 1,3,5-triethylbenzene, hexyl-, heptyl-, octyl-, nonyl-, decyl- and dodecylbenzene, hexamethylbenzene, hexaethylbenzene, diphenyl, 4,4'-dimethyldiphenyl, dibenzyl, diphenylmethane and 4,4'-dimethyl-diphenylmethane, halogen substituted aromatic hydrocarbons such as chlorobenzene, 1,2- and 1,4-dichlorobenzene, 1,4-diiodobenzene, 1,2,3- and 1,3,5-trichlorobenzene, 1,2,3,4- 1,2,3,5- and 1,2,4,5-tetrachlorobenzene, pentachlorobenzene, 1- and 2-fluoronaphthalene, 1- and 2-chloronaphthalene, 1- and 2-iodonaphthalene, and diphenyldichloromethane; nitro group containing aromatic hydrocarbons such as nitrobenzene, 3-nitrotoluene, 2-nitro-m-xylene, 5-nitro-m-xylene and 4-nitroanisol, aliphatic and aromatic ketones such as cyclohexanone, cycloheptanone, di-n-butylketone, di-n-amylketone, 1-tetralone, acetophenone, propiophenone, benzophenone, 3-methylbenzophenone, dodecanone-2 and tridecanone-2, sulfones and carboxylic acid esters such as sulfolane, diethylsulfone, phthalic acid dimethylester, phthalic acid diethylester, benzoic acid propylester, and lauric acid ethylester and ethers such as diethylene glycol dimethyl ether, diethylene glycol diethyl ether, diisoamylether, di-n-amylether, resorcinol dimethyl ether, resorcinol diethyl ether, phenyloctylether, phenylbenzylether, dibenzyl ether, diphenyl ether, α-methyl naphthyl ether and β-ethyl naphtyl ether.

Aryl urethanes, which are thermally decomposed into aryl isocyanates and alcohols in accordance with the process of this invention, have the general formula

Ar(NHCOOR)n in which Ar represents an aryl radical, R stands for a substituted or unsubstituted aliphatic or aromatic-aliphatic radical having 1 carbon atom to 20 carbon atoms, preferably 1 carbon atom to 10 carbon atoms, or a cycloaliphatic radical having 3 to 15 carbon atoms, preferably 3 to 7 carbon atoms, and in which n represents a whole number from 1 to 8 and higher, preferably 2 to 6.

Examples of aryl radicals include the radicals of aromatic monoamines such as aniline and substituted aniline, such as aniline, ortho-, meta- and/or para-hydroxy-, methoxy-, ethoxy-, propoxy-, isopropoxy-, N-butoxy-, isobutyoxy-, secondary butoxy and tertiary butoxyaniline substituted in the two, three and/or four position by a nitro-, methyl-, ethyl-, n-propyl, isopropyl-, n-butyl-, isobutyl-, secondary butyl-, tertiary butyl-group or a chlorine atom; by a benzoic acid alkylester having 1 to 4 carbon atoms in the alkyl radical and substituted by an amino group in the m- and/or p-position, N-alkoxycarbonylamino benzenes and -toluenes with 1 to 4 carbon atoms in the alkyl radical substituted by an amino group in the m- and/or p-position; α- and β-naphthylamine; aromatic diamines such as 1,3- and 1,4-diaminobenzene; 1,3-diaminobenzene substituted in the two or four position or 1,4-diaminobenzene, 1,5- and 1,8-diaminonaphthalene, 4,4'-diaminodiphenyl, 2,2'-, 2,4'- and 4,4'- diaminodiphenylmethane and the corresponding isomer mixtures and aromatic polyamines such as 1,3,5-triaminobenzene, 2,4,6-triaminotoluene and 1,3,5-triaminonaphthalene, polyphenyl polymethylene polyamines as well as mixtures of diaminodiphenylmethanes and polyphenyl polymethylene polyamines substituted in the two position by a nitro-, methyl-, ethyl-, n-propyl-, isopropyl-, n-butyl-, isobutyl-, secondary butyl-, tertiary butyl-, methoxy-, ethoxy-, n-propoxy-, isopropoxy-, n-butoxy-, isobutoxy-, secondary butoxy-, tertiary butoxy-group or a halogen atom, preferably a fluorine and/or chlorine atom. The above-mentioned substances are produced by familiar methods by the condensation of aniline and formaldehyde in the presence of preferably mineral acids as catalysts.

Preferably used as the aryl radicals, Ar, are the radicals of aromatic monoamines such as o-, m- and/or p-toluidine, o-, m- and/or p-anisidine, 3-hydroxyaniline, o-, m- and/or p-chloroaniline, 2,4-, 3,4- and 3,5-dichloroaniline, 2-nitro-4-aminotoluene, 4-nitro-2-aminotoluene, 2-nitro-6-aminotoluene and N-alkoxycarbonylarylamines having the formula

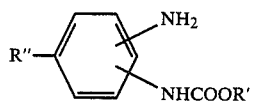

in which R' represents a methyl, ethyl, propyl, isopropyl, n-butyl, isobutyl, secondary butyl, or tertiary butyl radical and in which R" stands for a hydrogen or a radical R' as well as particularly aniline; of aromatic diamines such as 3,3'-di-toluene-4,4'-diamine, toluene 2,4, and -2,6 diamine as well as the corresponding isomer mixures, 2,2'-, 2,4'- and 4,4'-diaminodiphenylmethane and the corresponding isomer mixtures, 1,5- and 1,8-naphthalenediamine, and of polyamines such as mixtures of diaminodiphenylmethane and polyphenyl polymethylene polyamines.

Examples of the radical R include: the methyl, ethyl, n-propyl, isopropyl, n-butyl, isobutyl, secondary butyl, 2- and 3-methylbutyl, neopentyl, pentyl, 2-methylpentyl, secondary isoamyl, n-hexyl, 2-ethylhexyl, heptyl, n-octyl, n-nonyl, n-decyl, n-dodecyl, 2-phenylpropyl, benzyl, cyclopentyl, cyclohexyl, tertiary butylcyclohexyl, and bicyclo-(2,2,1)-heptyl radical. Preferably used as radical R is the methyl, ethyl, propyl, butyl, isobutyl, 2- and 3-methylbutyl, pentyl, n-hexyl, 2-ethylhexyl, n-heptyl, n-octyl, and cyclohexyl radicals.

Typical examples of aryl urethanes which can be decomposed according to the process of this invention include: N-phenylmethylurethane, N-phenylethylurethane, 3,5-dichlorophenylethylurethane, 4-methylphenylethylurethane, 2,4- and 2,6-toluene-di-methylurethane as well as the corresponding isomer mixtures; 2,4- and 2,6-toluene-di-ethylurethane, 2,4- and 2,6-toluene-di-butylurethane, 1,5-naphthylene-di-ethylurethane, 4,4'-, 2,4'- and 2,2'-methylenediphenyl-dimethylurethane, 4,4'-, 2,4'- and 2,2'-methylenediphenyl-diethylurethane, 4,4'-, 2,4'- and 2,2'-methylenediphenyl-dibutylurethane, 4,4'-, 2,4'- and 2,2'-methylenediphenyl-dihexylurethane as well as the corresponding isomer mixtures and mixtures of 4,4'-, 2,4'-, 2,2'-methylenediphenyl- and polymethylene-polyphenyl-di- and polymethylurethane, -ethylurethane, -butylurethane, and -hexylurethane.

The thermal decomposition of the aryl urethanes may take place in the vapor phase at a temperature between 300° C. and 600° C., preferably 330° C. and 380° C., as well as in the liquid phase at a temperature of between 175° C. and 350° C., preferably 220° C. and 320° C., on a batch-type basis or continuously under reduced, normal or increased pressure, for instance, in the vapor phase at pressures of 1 millibar to 1 bar, preferably 1 millibar to 100 millibars. The decomposition of the aryl urethanes and the isolation of the decomposition products by distillation of the alcohol and possibly the aryl isocyanate and/or the solvent may take place simultaneously or in sequence. As a rule, the decomposition in the vapor phase is carried out under reduced pressure, the maximum of which, at the above-mentioned temperature range, is equal to the pressure at which the reaction mixture boils. In the case of simultaneous decomposition in the liquid phase and isolation, an advantageous temperature/pressure relationship is one that corresponds with the boiling point of the lowest boiling component of the bottom fraction. In a closed system, for instance in a tube reactor, the decomposition advantageously takes place without increasing the system pressure.

The raw materials may be fed into the reactor in vapor, liquid or solid form, such as in a powder, as a suspension or as a solution in an inert solvent. The reactor is maintained at a predetermined certain temperature at a specified pressure. For instance, a vapor, liquid or solid aryl diurethane, corresponding with 0.1 urethane equivalent per liter an hour to 20 urethane equivalents per liter an hour, preferably 1 urethane equivalent per liter an hour to 10 urethane equivalents per liter an hour, is reacted at a temperture of 300° C. to 400° C., preferably 330° C. to 380° C., and a pressure of 1 millibar to 1 bar, preferably 1 millibar to 100 millibars, in a tube reactor charged with zinc shavings. The aryl diisocyanate, alcohol, and possibly unreated aryl diurethane is advantageously fractionally condensed via a column by adding an inert solvent, the boiling point of which is between the boiling point of the alcohol and that of the isocyanate.

In one embodiments, the solution of a di- and/or polyurethane and an inert solvent may be directed through a tube reactor charged with zinc or aluminum granules at a temperature of 175° C. to 350° C., preferably 220° C. to 320° C., and the product may subsequently be directed into a column or through a cascade of several operating reactors and separating columns in alternating sequence in order to facilitate the isolation of the product.

According to one preferred version, the solution is continuously fed into a separating reactor and/or a reactor cascade with the alcohol simultaneously being isolated, possibly with the aid of a stripping agent, for instance, an inert gas or an intermediate boiler, and the aryl isocyanate being isolated via one or more separating columns with the solvent which is discharged as bottom fraction, being refluxed.

According to another preferred process variation, the aryl-di- and/or -polyurethane, for instance, crude MDU, can be decomposed in the liquid phase in a suitable solvent as described above. At the same time, the alcohol may be removed by distillation with the solvent being refluxed. Consequently, the solvent is removed from the sump by careful distillation, possibly by stripping with a short residence time, with the aryl-di- and/or -polyisocyanates being refluxed and the aryl-di- and/or -polyisocyanate discharged as bottom fractions.

It was shown to be advantageous to remove part of the aryl diisocyanate, diphenylmethane-diisocyanate, for instance, 5 to 10 percent by weight, together with the solvent, by means of distillation and to recycle these substances together with the solvent to the decomposition reactor.

According to the process of this invention, aryl isocyanates of high purity and improved yields can be produced on a profitable basis. The advantages of the process according to this invention become particularly clear in the example of crude MDI, the thermal decomposition of which has not been previously described by example.

The aryl monoisocyanates obtained in accordance with this invention are valuable intermediates for the manufacture of pesticides, dyes and auxiliaries; the aryl-di- and/or -polyisocyanates are preferably used for the manufacture of polyurethane plastics.

The following examples will further illustrate the various aspects of the invention. These examples, however, are not to be considered as limiting the invention. Where not otherwise specified throughout this specification and claims, temperatures are in degrees centigrade, and parts, percentages and proportions are by weight.

EXAMPLE 1

Twenty parts of N-phenylmethylurethane were dissolved in 30 parts of dibenzylnaphthalene and fed at a rate of 320 liters per liter of reaction volume an hour into a mixing reactor having a volume of 150 milliliters with overflow of quartz glass, charged with 5 parts of aluminum granules having a grain size of 1–3 millimeter diameter and heated to a temperature of 330° C. For collecting the discharge products in the vapor phase, two cooling traps were connected with the reactor. 6.9 Parts of phenylisocyanate were condensed in the first water-cooled vessel. Methanol formed by the separation was condensed in the second vessel which was cooled with dry ice. Another 7.3 parts of phenylisocyanate were shown in the separating solvent by means of gas chromatography (using the method of the "internal standard"). Accordingly, 14.2 parts of phenylisocyanate were produced (97.4 percent of theory relative to reacted phenylurethane). By means of gas chromatography, 1.5 parts of raw material were shown in the separation solvent so that 92.5 percent phenylmethylurethane was converted.

COMPARISON EXAMPLE

The procedure of Example 1 was followed except that the catalyst was omitted.

Only 13.3 percent of the phenylmethylurethane fed was reacted to produce 2.0 parts of phenylisocyanate (95.4 theoretical percent relative to reacted phenylmethylurethane).

EXAMPLES 2-9

The procedure of Example 1 was followed varying the catalyst material and the feed aryl urethanes. The results are listed in Table 1.

TABLE 1

| Example No. | Aryl Urethane | Catalyst | Conversion of Urethanes % | Isocyanate Yield % |
|---|---|---|---|---|
| 2 | C$_6$H$_5$—NHCO$_2$CH$_3$ | Iron | 69.3 | 97.4 |
| 3 | C$_6$H$_5$—NHCO$_2$CH$_3$ | Cobalt | 61.0 | 93.8 |
| 4 | C$_6$H$_5$—NHCO$_2$C$_2$H$_5$ | Nickel | 80.1 | 97.7 |
| 5 | C$_6$H$_5$—NHCO$_2$CH$_3$ | Chromium | 86.3 | 99.0 |
| 6 | C$_6$H$_5$—NHCO$_2$CH$_3$ | Titanium | 79.3 | 97.9 |
| 7 | C$_6$H$_5$—NHCO$_2$CH$_3$ | Zinc | 92.8 | 98.6 |
| 8 | 3,5-Cl$_2$-C$_6$H$_3$—NHCO$_2$CH$_3$ | Aluminum | 97.3 | 99.4 |
| 9 | CH$_3$—C$_6$H$_4$—NHCO$_2$CH$_3$ | Zinc | 77.1 | 89.9 |

EXAMPLE 10

Via a powder metering device, 86 parts of 2,4-bis(methoxycarbonylamino)toluene were continuously fed at a rate of approximately 500 liters per liter of reaction volume an hour into a tube reactor of quartz glass filled with zinc shavings and heated to 350° C. A pressure of 10 millibars to 15 millibars was maintained in the reactor. The escaping decomposition gases were fractionally condensed with 61 parts of toluene diisocyanate (TDI) (97.0 theoretical percent relative to the feed 2,4-bis(methoxycarbonylamino)toluene) being obtained in a water-cooled vessel.

EXAMPLE 11

Eighty parts of 4,4'-bis(hexoxycarbonylamino)diphenylmethane were dissolved in 80 parts of 1,2,4,5-tetramethylbenzene with a feed rate of 100 liters per liter of reaction volume an hour. This solution was fed into a tube reactor of quartz glass filled with aluminum shavings and heated to 350° C. in which a pressure of 5 millibars to 10 millibars was maintained. The hexanol resulting from the decomposition was separated in gaseous form and condensed with evaporated tetramethylbenzene in a water-cooled vessel. 65 Parts of a solution of 32 parts of methylene diphenyl diisocyanate (72.6 theoretical percent relative to complete reaction of 4,4'-bis(hexoxycarbonylamino)diphenylmethane) and 16 parts of 4-(hexoxycarbonylamino)-4'-isocyanato-diphenylmethane and 4-isocyanato-4'-hexoxycarbonylamino-diphenylmethane in tetramethylbenzene were obtained as reactor discharge. The decomposition of 4,4'-bis(hexoxycarbonylamino)diphenylmethane was quantitative.

EXAMPLE 12

Via a powder metering device, 25 parts of 1,5-bis(ethoxycarbonylamino)naphthalene were fed at a rate of 450 liters per liter of reaction volume an hour into a tube reactor filled with zinc shavings and heated to 350° C. A pressure of 1 millibar to 3 millibars was maintained in the separating reactor. The escaping decomposition gases were fractionally condensed. In a first water-cooled vessel, 14 parts of 1,5-naphthalene diisocyanate (NDI) were obtained (80.5 theoretical percent relative to feed urethane). The melting point was 129° C. to 132° C.

EXAMPLE 13

170 Parts of 2,4-di-(butoxycarbonylamino)-toluene were dissolved in 350 parts of dodecylbenzene. With a feed rate of 300 liters per liter of reaction volume an hour, this solution was fed into a separating reactor of a quartz glass filled with an aluminum graulate having a grain size of 1 millimeter to 3 millimeters and heated to a temperature of 320° C. Using 8 liters of nitrogen per liter of reaction mixture an hour as a stripping agent, the butanol resulting from the reaction was separated in a gaseous form and condensed in a vessel cooled with dry ice. This resulted in 443 parts of reaction discharge from which 81 parts of 2,4-toluene diisocyanate (88.2 theoretical percent relative to reacted 2,4-di-(butoxycarbonylamino)-toluene) were obtained by distillation at a temperature between 76° C. and 82° C. and a pressure of 0.2 millibar. The raw material had reacted completely. A mixture of refluxable 2-butoxycarbonylamino-4-isocyanatotoluene and 4-(butoxycarbonylamino)-2-isocyanatotoluene was proven in the distillation residue by means of gas chromatography.

EXAMPLE 14

Ten parts of a commercially available "crude MDI" mixture was reacted with hexanol to form a mixture of methylene-diphenyl-dihexylurethanes and methylene-polyphenyl-polyhexylurethanes and this mixture is referred to as "comparison product". Another 100 parts of the same commercially available "crude MDI" mixture was now reacted with methanol to form a mixture of methylene-diphenyl-dimethylurethane and poly-methylene-polyphenyl-polymethylurethane. 120 Parts of this urethane were dissolved in 400 parts of decylbenzene and this solution fed at a rate of 300 liters per liter of reaction volume an hour into a tube reactor of quartz glass filled with zinc shavings and heated to a temperature of 320° C. The methanol formed by the decomposition was isolated in gaseous form and condensed in a vessel cooled with dry ice. 510 Parts of reaction discharge were obtained from which the solvent was almost completely removed by distillation. The reaction discharge was mixed with 100 parts of hexanol. This resulted in a solution of methylene-diphenyl-dihexylurethanes and polymethylene-polyphenyl-polyhexylurethanes, the high pressure liquid chromatogram of which was identical with that of the "comparison product".

The embodiments of the invention in which an exclusive privilege or property is claimed are defined as follows:

1. A process for making aryl isocyanates comprising thermally decomposing aryl urethanes at a temperature between 175° C. and 600° C. in the presence of a catalyst, present in a heterogeneous phase, said catalyst being a metal selected from the group consisting of zinc and aluminum.

2. The process of claim 1 comprising decomposing the aryl urethanes in a liquid phase in a solvent at a temperature between 175° C. and 350° C. in the presence of a catalyst selected from the group consisting of zinc and aluminum which is present in the heterogeneous phase.

3. The process of claim 2 in which the aryl urethanes are decomposed at a temperature between 220° C. and 320° C.

4. The process of claim 1 in which the catalyst is a catalyst with a large surface area.

5. The process of claim 2 in which the catalyst is a catalyst with a large surface area.

6. The process of claim 1 comprising decomposing the aryl urethanes in a vapor phase at a temperature between 300° C. and 600° C. in the presence of a catalyst selected from the group consisting of zinc and aluminum which is present in the heterogeneous phase.

7. The process of claim 6 in which the aryl urethanes are decomposed at a temperature between 330° C. and 380° C.

8. The process of claim 6 in which the catalyst is a catalyst with a large surface area.

9. The process of claim 1 wherein aryl-di- and/or -polyurethanes are used as aryl urethanes.

10. The process of claim 1 wherein aryl mono urethanes are used as aryl urethanes.

11. The process of claim 1 wherein the aryl urethane is a mixture of a diphenylmethane diurethane and a polyphenyl polymethylene polyurethane.

12. The process of claim 4 wherein the aryl urethane is a mixture of diphenylmethane diurethane and a polyphenyl polymethylene polyurethane.

13. The process of claim 5 wherein the aryl urethane is a mixture of a diphenylmethane diurethane and a polyphenyl polymethylene polyurethane.

14. The process of claim 8 wherein the aryl urethane is a mixture of a diphenylmethane diurethane and a polyphenyl polymethylene polyurethane.

* * * * *